United States Patent [19]

Banchereau et al.

[11] Patent Number: 5,162,224

[45] Date of Patent: Nov. 10, 1992

[54] MONOCLONAL ANTIBODIES SPECIFIC FOR B CELLS AND HTLV-I TRANSFORMED T CELLS

[75] Inventors: Jacques F. Banchereau, Ecully; Alain Valle, Lyons LaDuchere, both of France

[73] Assignee: Schering Corporation, Kenilworth, N.J.

[21] Appl. No.: 375,421

[22] Filed: Jul. 3, 1989

[30] Foreign Application Priority Data

Jul. 13, 1988 [FR] France .................. 88 09588

[51] Int. Cl.⁵ ............................... C12N 5/20
[52] U.S. Cl. .................... 435/240.27; 530/388.73; 435/7.24; 435/813
[58] Field of Search ............ 435/240.27, 813; 424/85.8; 530/387, 388.73

[56] References Cited

U.S. PATENT DOCUMENTS

| | | | |
|---|---|---|---|
| 4,692,405 | 9/1987 | Freedman et al. | 435/7.23 |
| 4,831,117 | 5/1989 | Uckun | 530/387 |
| 4,845,198 | 7/1989 | Urdal et al. | 530/387 |
| 4,855,235 | 8/1989 | Takahashi et al. | 435/240.27 |

OTHER PUBLICATIONS

T. Yokochi et al., *J. Immunology*, 1982, vol. 128, pp. 823–827.

A. S. Freedman et al., *J. Immunology*, 1987, vol. 139, pp. 3260–3267.

*Primary Examiner*—Esther L. Kepplinger
*Assistant Examiner*—Donna C. Wortman
*Attorney, Agent, or Firm*—John H. G. Blasdale; James R. Nelson; Edward H. Mazer

[57] ABSTRACT

The present invention relates to a monoclonal antibody- and to the hybridoma that produces it-specific for a surface antigen of activated B cells and T cells transformed by the virus HTLV-I. The hybridoma has been deposited with the European Collection of Annimal Cell Cultures (ECACC) under the number 88062301.

2 Claims, No Drawings

MONOCLONAL ANTIBODIES SPECIFIC FOR B CELLS AND HTLV-I TRANSFORMED T CELLS

FIELD OF THE INVENTION

The invention relates generally to monoclonal antibodies and their associated hybridomas, and more particularly to monoclonal antibodies specific for an antigen expressed by both retrovirally transformed human T cells and activated human B cells. The antigen is also expressed by leukemic B lymphocytes.

BACKGROUND

During a humoral immune response, resting B cells become activated, divide several times, and undergo terminal differentiation into plasma cells secreting different classes and subclasses of immunoglobulins. Frequently the change in the state of B cells, e.g. from resting to proliferating, from proliferating to secreting, or the like, can be correlated with changes in cell surface molecules, and these latter changes can be identified with monoclonal antibodies specific for the surface molecules or antigens; e.g. Zola, Immunol. Today, Vol. 8, pgs. 308-315 (1987). Such surface antigens can sometimes provide an approach for diagnosis and treatment, when a disease state is associated with the presence of cell types positive for particular surface antigens; e.g. Ramsay et al., Blood, Vol. 66, pgs. 508-513 (1985), "Autologous bone marrow transplantation for patients with acute lymphoblastic leukemia in second or subsequent remission: results of bone marrow treated with monoclonal antibodies BA-1, BA-2, and BA-3 plus complement" (treatment of common acute lymphoblastic leukemia (CALL) with antibodies specific for a CALL-specific antigen).

T cells are a class of lymphocytes essential for the activation of B cells during an immune response. Several important diseases are associated with depleted or non-functional T cell populations. At least two such diseases, AIDS and adult T cell leukemia (ATL), are caused by retroviruses, designated HTLV-III (now HIV) and HTLV-I, respectively; e.g. Broder et al., Ann. Rev. Immunol., Vol. 3, pgs. 321-336 (1985). ATL cells, like many other neoplastic cells, are associated with distinctive patterns of surface antigen expression, which sometimes provide a means for diagnosis or treatment; e.g. Jaffe et al., chapter 120, in Rose et al., eds., Manual of Clinical Laboratory Immunology, 3rd Ed. (American Society for Microbiology, Washington, D.C., 1986). Clearly, the identification of an additional surface antigen associated with particular disease states, and the development of monoclonal antibodies thereto, would improve available diagnostic protocols.

SUMMARY OF THE INVENTION

The invention includes a monoclonal antibody specific for a surface antigen of activated B cells, and a hybridoma producing such antibodies. The hybridoma of the invention is referred to herein as clone 104, and its antibody is referred to herein as Mab 104. A sample of clone 104 was deposited with the European Collection of Animal Cell Cultures on Jun. 23, 1988, under accession number 88062301. One aspect of the invention is the discovery that the B cell surface antigen recognized by Mab 104 is expressed by HTLV-I infected T cells. Thus, the invention includes methods for detecting T cells infected with HTLV-I. We have indeed also discovered that this antigen is expressed by leukemic B lymphocytes, especially by freshly-isolated leukemic B lymphocytes. Therefore, the invention further includes methods of detecting leukemic B lymphocytes, and in particular methods for eliminating leukemic cells. The monoclonal antibody of the present invention could therefore serve as a therapeutic agent for eliminating leukemic cells in vivo or by ex vivo purging of bone marrow aspirates or cultures.

DETAILED DESCRIPTION OF THE INVENTION

The invention includes a monoclonal antibody Mab 104 which is specific for a surface antigen on human B cells activated by anti-IgM antibody. Mab 104 is useful as a marker for HTLV-I transformed T cells.

An object of the invention is therefore to provide a process for the detection of activated B lymphocytes or of T-cells transformed by HTLV-I.

Further objects of the invention are to provide methods of detecting leukemic B lymphocytes, and in particular methods for eliminating leukemic cells.

Other objects of the present invention are to provide a monoclonal antibody that can serve as a therapeutic agent for eliminating leukemic cells, especially leukemic B or T lymphocytes, by in vivo or by ex vivo purging of bone marrow aspirates or cultures; and to provide corresponding methods of use and treatment using the monoclonal antibody of the present invention.

Hybridoma clone 104 was produced as follows. Eight week-old BALB/c mice were injected i.p. four times at weekly intervals with approximately $50 \times 10^6$ Jijoye cells (a human Burkitt lymphoma cell line available from the American Type Culture Collection (ATCC), Rockville, Md., under accession number CCL87). Three days after the last injection, spleen cells were collected and fused with NS1 myeloma cells (available from the ATCC under accession number TIB 18) at a 5:1 ratio (spleen cells: NS1 cells) with the use of polyethylene glycol 1000 (available from Merck, Darmstadt, West Germany). After overnight incubation at 37° C. in a 50 ml flask in complete RPMI 1640 medium containing 10% heat-inactivated fetal bovine serum, 2mM glutamine, 100 IU/ml penicillin and 100 µg/ml streptomycin (e.g. available from Flow Labs, Irvine, Scotland), the cell suspension was distributed in 24-well plates in hypoxanthine-azaserine medium. Hybridoma supernatants were screened for their ability to bind to Jijoye cells, tonsil mononuclear cells and anti-IgM activated B cells obtained as described below. The selected hybridomas were cloned and subcloned by limiting dilution. In this way a line of hybridoma cells, 104, was obtained.

The monoclonal antibody according to the invention was obtained as follows:

For ascites production, BALB/c mice were injected i.p. with 0.5 ml of pristane (Aldrich, Milwaukee Wis.). Ten days later, $10^7$ hybridoma cells were injected i.p. and ascitic fluid was collected 2 to 3 weeks later. The ascitic fluid was centrifuged at $30,000 \times g$ for 30 min at 4° C. to remove lipids and cellular debris. Monoclonal antibodies were isolated from ascitic fluid by high performance liquid chromatography (HPLC) with an anion-exchange column (DEAE 5PW : Waters Associates, Millipore Corp., Milford, Mass.). Alternatively, monoclonal antibodies were purified from culture supernatants by affinity chromatography on protein A columns (Biorad, Richmond, Calif.) using standard techniques. The isotype of Mab 104 was determined by Ouchterlony analysis with the use of polyclonal antibodies specific for mouse Ig classes and subclasses (e.g. available from Zymed, South San Francisco, Calif.).

Cells used for inoculation, fusion, and screening were obtained as follows. Mononuclear cell suspensions were obtained from tonsils, spleens, peripheral blood, cord blood or bone marrow aspirates. Tonsils and spleens were dissociated on a "mesh-wire" in phosphate-buffered saline (PBS), pH 7.2, to obtain single-cell suspensions. The organ cell suspensions or diluted blood were layered on a Ficoll-Hypaque gradient and, after centrifugation, cells at the interface were harvested and washed three times with PBS. To obtain purified B cell populations, T cells were removed from the mononuclear cells by twice rosetting with 2-aminoethylisothiouronium-bromide-treated sheep erythrocytes. Monocytes were depleted by adhering $250 \times 10^6$ T-cell-depleted cells to plastic flasks (Corning, Oxnard, Calif.) containing 25 ml RPMI 1640 with 10% fetal calf serum for 1 hour at 37° C. The tonsilar B cell preparations contained more than 95% B cells as determined by staining cells with a mouse anti human B cell-specific monoclonal antibody, B1(CD20) (Coulter, Hialeah, Fla.) and fluorescein-conjugated F(ab')$_2$ goat anti-mouse Ig (Grub); less than 1% T cells as determined by the Leu-5 (CD2) monoclonal antibody (Becton Dickinson, Mountain View, Calif.), less than 1% monocytes as determined by the Leu M3 (CD15) monoclonal antibody (Becton Dickinson). Purified B cells were separated into in vivo preactivated B cells (low density) and resting B cells (high density) using a discontinuous gradient of Percoll (Pharmacia, Uppsala, Sweden) consisting of four solutions with densities of 1.075; 1.070; 1.060 and 1.055 g/ml. Resting B cells were recovered in the pellet, below the solution of Percoll of the highest density. Large in vivo preactivated B cells were recovered at the interface between Percoll densities of 1.060 and 1.070 g/ml.

B cells preactivated by anti-IgM antibodies were obtained as follows. Purified B cells (low and high density) were cultured at $10^6$ cells/ml in Iscove's medium enriched with 50 μg/ml human transferrin, 0.5% bovine serum albumin, 5 μg/ml bovine insulin, 2% heat-inactivated fetal calf serum, and oleic, linoleic, and palmitic acids (Sigma) as described by Defrance et al., *J. Immunol.*, Vol. 1390, pgs. 1135-1142 (1987). Cultures were adjusted to $2 \times 10^6$ cells/ml and were stimulated for 24 hours by anti-IgM antibody (10 μg/ml) insolubilized by attachment to beads. After such activation, B cells were harvested and centrifuged over a Ficoll/Hypaque gradient to remove nonviable cells and anti-IgM beads. For screening, the activated B cells were resuspended at $1 \times 10^6$ cells/ml in the enriched Iscove's medium which was dispensed in 50 μl aliquots into wells of microtiter trays. Mab 104 was found to be of the immunoglobulin subclass IgG$_1$.

The specificity of Mab 104 was characterized by flow cytometry. A panel of different cell types was prepared and fluorescently stained. Fluorescence staining was performed in microtrays. Cells ($5 \times 10^5$ in 50 μl) were incubated with 100 μl of hybridoma supernatant or 10 μl of purified Mab appropriately diluted. After two washes, cells were incubated with fluoresceinated F(ab')$_2$ fragments of goat anti-mouse Ig for 30 min at 4° C. (1/100 diluted). Cell staining was analyzed with FACS 440 (Becton Dickinson, Sunnyvale, Calif.) equipped with a 5-W argon laser running at 488 nm, 0.5 W.

Table I shows the reactivity of Mab 104 with various mononuclear cell preparations. It can be seen that significant binding only occurs with activated B cells. Table II shows the reactivity of Mab 104 with various human cell lines. Strong binding only occurs with Burkitt lymphoma cells or EBV-transformed lymphoblastoid cell lines. Table III shows the reactivity of Mab 104 with HTLV-I transformed T cell lines and non-HTLV-I transformed T cell lines. Strong binding occurs only on the HTLV-I transformed T cells.

TABLE I

Reactivity[a] of Mab 104 with various mononuclear cell preparations

|  | Mab 104 | CD 20 |
|---|---|---|
| Blood mononuclear cells | 3 ± 2 | 10 ± 4 |
| 3 days PHA blasts[b] | 4 ± 2 | 8 ± 4 |
| Tonsil mononuclear cells | 5 ± 4 | 56 ± 4 |
| Tonsil B cells | 9 ± 5 | 98 ± 2 |
| Anti IgM activated B cells | 39 ± 24 | 97 ± 4 |
| Spleen mononuclear cells | 4 ± 3 | 42 ± 5 |
| Speen B cells | 11 ± 3 | 97 ± 2 |
| Bone marrow mononuclear cells | 1 ± 1 | 6 ± 2 |
| Cord blood mononuclear cells | 1 ± 1 | 11 ± 3 |

[a]reactivity was assessed as a mean percentage of positive cells ± SD by indirect immunofluorescence and flow cytometry.
[b]blood mononuclear cells stimulated for 3 days in culture with phytohemagglutinin (PHA), using standard protocols, e.g. Carpenter, chapter 43, in Rose et al., eds. (cited above).

TABLE II

| Cell Lines | Staining[a] with Mab 104 |
|---|---|
| T cell lines: | |
| Molt 4 | − |
| Jurkat | − |
| CEM | − |
| Myelomonocytic cell lines: | |
| HL60 | − |
| U937 | − |
| KG1 | − |
| Burkitt lymphoma cell lines: | |
| Jijoye | +++ |
| Daudi | +++ |
| EBV-transformed lymphoblastic cell lines | |
| RPMI 8866 | +++ |
| Myelomatous cell line: | |
| RPMI 8226 | + |
| U266 | − |

[a]− not detectable; + weak reactivity; +++ strong reactivity.

TABLE III

| Cell Lines | Reactivity[a] run 1 | run 2 |
|---|---|---|
| MLA 144 (gibbon lymphoma, ATCC TIB 201) | 26.6% | 20.3% |
| HUT 102 (human T cell lymphoma carrying HTLV-I, ATCC TIB 162) | 96.6% | 95.9% |
| T cell clone 827[b] | 3% | 5% |
| HTLV-I transformed T-cell clone 827 | 65% | 68.6% |

[a]Reactivity was assessed as the percentage of positively staining cells measured by flow cytometry.
[b]Clone of T-cells whose growth is dependent upon interleukin-2.

The antigen for which Mab 104 is specific was characterized as follows. Approximately $5 \times 10^7$ Jijoye cells were washed twice with PBS containing 1 mM phenylmethylsulfonyl fluoride (PMSF:Sigma) and then were resuspended in 2 ml PBS, 0.5 millicurie of Na$^{125}$I (Oris, Saclay, France), 100 μl lactoperoxidase at 5 mg/ml (Calbiochem-Behring, La Jolla, Calif.), and 50 μl H$_2$O$_2$ (0.03% in water) were added. After 3 min of gentle agitation at room temperature, another 100 μl of lactoperoxidase and 50 μl of H$_2$O$_2$ were added. The suspension was again agitated for 3 min at room temperature. The addition and agitation were repeated once again, and the cells were finally washed with PBS containing 5 mM KI. Labeled cells were resuspended at $5 \times 10^6$/ml in PBS containing 0.5% Nonidet p40 (NP-40). 1 mM PMSF, 0.01M benzamidine hydrochloride, 0.05M aminocaproic acid, 20 mM iodoacetamide, 10 μg/ml leupeptin, 1 μg/ml pepstatin, and 100 μg/ml soybean trypsin inhibitor (all from Sigma) were added and the mixture was incubated at 0° C. for 20 min. The lysate was then centrifuged at $3000 \times g$ for 20 min, and the supernatant was clarified by centrifugation at $100,000 \times g$ for 30 min. The lysates were precleared overnight with a nonrelated Mab. Then a rabbit anti-mouse Ig coupled to formalized *Staphylococcus aureus* strain Cowan (Pansorbin; Calbiochem) was added. After centrifugation, the lysate was subjected to immunoprecipitation with the relevant Mab.

Immunoprecipitation was carried out by incubating 100 μl of radiolabeled lysate with 4 μg of purified Mab for 14 hr at 4° C. The immune complexes were precipitated with 20 μl rabbit anti-mouse Ig complexed with Pansorbin for 20 min at room temperature and 1 hr at 4° C. The complexes were eluted by boiling in pH 6.8 SDS buffer containing 3% SDS, 15% glycerol, and 0.01% bromphenol blue, with or without 5% 2-mercaptoethanol, and were electrophoresed on SDS-polyacrylamide gels. For autoradiography, Kodak XAR-5 film was used in combination with intensifier screens (Kodak-Eastman, Paris, France). The antigen recognized by Mab 104 was pronase-sensitive but not trypsin-sensitive, indicating a proteinic nature. The antigen recognized by Mab 104 could be precipitated from labelled RPMI 8866 or Jijoye cell lysates. Antigen 104 migrated under both reducing and non-reducing conditions as a diffuse band of 45000-60000 daltons, suggesting heterogeneity in glycosylation.

Monoclonal antibodies of the invention are produced by culturing clone 104 using standard culturing procedures; e.g., Schreier, et al., *Hybridoma Techniques* (Cold Spring Harbor Laboratory, N.Y., 1980); Hurrell, Ed., *Monoclonal Hybridoma Antibodies: Techniques and Applications* (CRC press, Boca Raton, 1982); Campbell, *Monoclonal Antibody Technology* (Elsevier, N.Y., 1984); and Gratzner, U.S. Pat. No. 4,529,700, which is incorporated herein by reference. Briefly, clone 104 can be propagated in either of two standard ways. A sample of the hybridoma can be injected into a histocompatible animal of the type that was used to provide the somatic and myeloma cells for the fusion in which the hybridoma was created, e.g., BALB/c mice. The injected animal develops tumors secreting the specific monoclonal antibody produced by the hybridoma. The body fluids of the animal, such as serum or ascites fluid, can be tapped to provide monoclonal antibodies in high concentration. Alternatively, a hybridoma may be propagated in vitro in laboratory culture vessels; the culture medium, also containing high concentrations of the single specific monoclonal antibody, can be harvested and purified by standard protocols; e.g. Tijssen, *Practice and Theory of Enzyme Immunoassays* (Elsevier, Amsterdam, 1985).

Mab 104 in conjunction with a labeling means can be used as a component in a variety of assays for detecting HTLV-I infected T cells. Preferably Mab 104 is used to assay peripheral blood for the presence of HTLV-I infected T cells by flow cytometry. The principles and operation of such instruments are well-established, and several flow cytometers suitable for use with the invention are available commercially; e.g., *Flow Cytometry and Sorting*, Melamed et al., Eds. (John Wiley & Sons, N.Y., 1979); *Flow Cytometry; Instrumentation and Data Analysis*, Van Dilla et al., Eds. (Academic Press, N.Y., 1985); Mairhead et al., "Flow Cytometry: Present and Future", *Bio/Technology*, Vol. 3, pgs. 337-356 (1985); and U.S. Pat. Nos. 3,710,933, 3,380,584, and 4,325,706, which are all incorporated herein by reference for the descriptions of flow cytometers. Other kinds of instruments such as those used in analytical cytology could also be used in accordance with the invention; e.g. Ploem et al., "An Automated Microscope for Quantitative Cytology (Combining Television Image Analysis and Stage Scanning Microphotometry)", *J. Histochem. Cytochem.*, Vol. 27, pgs. 136-143 (1979).

When Mab 104 is used with a flow cytometer, a fluorescent labeling means is preferred. Many direct and indirect fluorescent labeling means are available; e.g., Haugland, *Handbook of Fluorescent Probes and Research Chemicals* (Molecular Probes, Inc., Junction City, Oreg., 1985) provides an extensive review of fluorescent molecules that can be conjugated with antibodies. Preferred fluorescent dyes include fluorescein, Texas Red, tetramethylrhodamine, and phycoerythrin. Such dyes are available commercially and are linked to antibodies by standard techniques; e.g. Wood et al., *J. Immunol.*, Vol. 95, pgs. 225-229 (1965), and Oi et al., *J. Cell Biol.*, Vol. 93, pgs. 981-986 (1982). At least two modes of indirect labeling are preferred: (1) bound Mab 104 is reacted with a second directly-labeled heterologous anti-immunoglobin antibody, and (2) Mab 104 is covalently linked to one or more biotin molecules, the biotinylated antibody is reacted with a target cell, and then the bound Mab 104 is reacted with directly-labeled avidin, or streptavidin. The avidin-biotin technique is well known, e.g. Bayer et al., "The Use of the Avidin-Biotin Complex as a Tool in Molecular Biology," in Glide, Ed., *Methods of Biomedical Analysis*, Vol. 26, pgs. 1-45 (John Wiley, N.Y., 1980).

Mab 104 can also be used for eliminating leukemic B lymphocytes from bone marrow cells, by the step of contacting bone marrow containing said lymphocytes with said monoclonal antibody, followed by removal or killing of the cells bearing the antibody. The cells bearing the antibody (the opsonized cells) can be killed or removed by several standard methods: thus, after the contacting step the bone marrow cells can be incubated with complement to lyse and kill opsonized cells; or they can be incubated with magnetic beads coated with an antibody specific for mouse immunoglobulins, and the beads and the opsonized cells bonded thereto can then be separated out with a magnet. When the contacting is effected ex vivo, the purified bone marrow cells can then be restored to their donor.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A monoclonal antibody specific for a B cell surface antigen of activated B cells and HTLV-I transformed cells, which is produced by a hybridoma cell line deposited with the European Collection of Animal Cell Cultures (ECACC) under the deposit accession number 88062301.

2. The hybridoma cell line deposited with the European Collection of Animal Cell Cultures under the deposit accession number 88062301.

* * * * *